United States Patent [19]

Meilland

[11] Patent Number: Plant 7,289

[45] Date of Patent: Aug. 7, 1990

[54] ROSE PLANT—MEIFRONY VARIETY

[75] Inventor: Alain A. Meilland, Antibes, France

[73] Assignee: The Conard-Pyle Company, West Grove, Pa.

[21] Appl. No.: 354,281

[22] Filed: May 19, 1989

[51] Int. Cl.[5] ..... A01H 5/00
[52] U.S. Cl. ..... Plt./18
[58] Field of Search ..... Plt./18, 19, 11

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which forms in abundance semi-double blossoms of long vase life which are French rose in coloration and edged and suffused with neyron rose. The buds possess an elegant conical and elongated configuration. The plant exhibits an upright growth habit, very vigorous vegetation, and is well suited for greenhouse forcing for cut flower production. Good resistance to fungal diseases also is manifest.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Emily Post variety (U.S. Plant Pat. No. 3,749). The male parent (i.e., the pollen parent) of the new variety was the Jelpirofor variety (nonpatented in the United States). The parentage of the new variety can be summarized as follows:

Emily Post × Jelpirofor.

The seeds resulting from the above pollination were sown and 5 small plants were obtained which were physically and biologically different from each other. Selective study resulted in the identification of a single plant of the new variety.

It was found that the new variety of Hybrid Tea rose plant of the present invention possesses the following combination of characteristics:

(a) forms elegant conical and elongated buds,
(b) forms in abundance semi-double blossoms which are French rose in coloration and edged and suffused with neyron rose,
(c) exhibits an upright growth habit,
(d) forms vigorous vegetation,
(e) is well adapted for greenhouse forcing, and
(f) exhibits good resistance to cryptogamic diseases.

The new variety well meets the needs of the horticultural and is particularly well-suited for the production of cut flowers.

The new variety has been found to undergo asexual propagation by a number of routes, including budding, grafting, cuttage, etc. The characteristics of the new variety have been found to be strictly transmissible by such asexual propagation fron one generation to another.

The new variety has been named the Meifrony variety. cl BRIEF DESCRIPTION OF THE PHOTOGRAPH The accompanying photograph shows as nearly true as it is reasonably possible to make the same, in a color illustration of this character, typical specimens of the plant parts of the new variety. The rose plants of the new variety were two years of age and observed during November while grafted on *Rosa indica* understock and growing in greenhouses at Cap d'Antibes, France.

FIG. 12 illustrates a specimen of a section of a flowering stem;

DETAILED DESCRIPTION

Figures 1, 2, 3, 4, 5, 6, 7, 8, 9, 10, 11, 13, 14, 15, 16, 17:
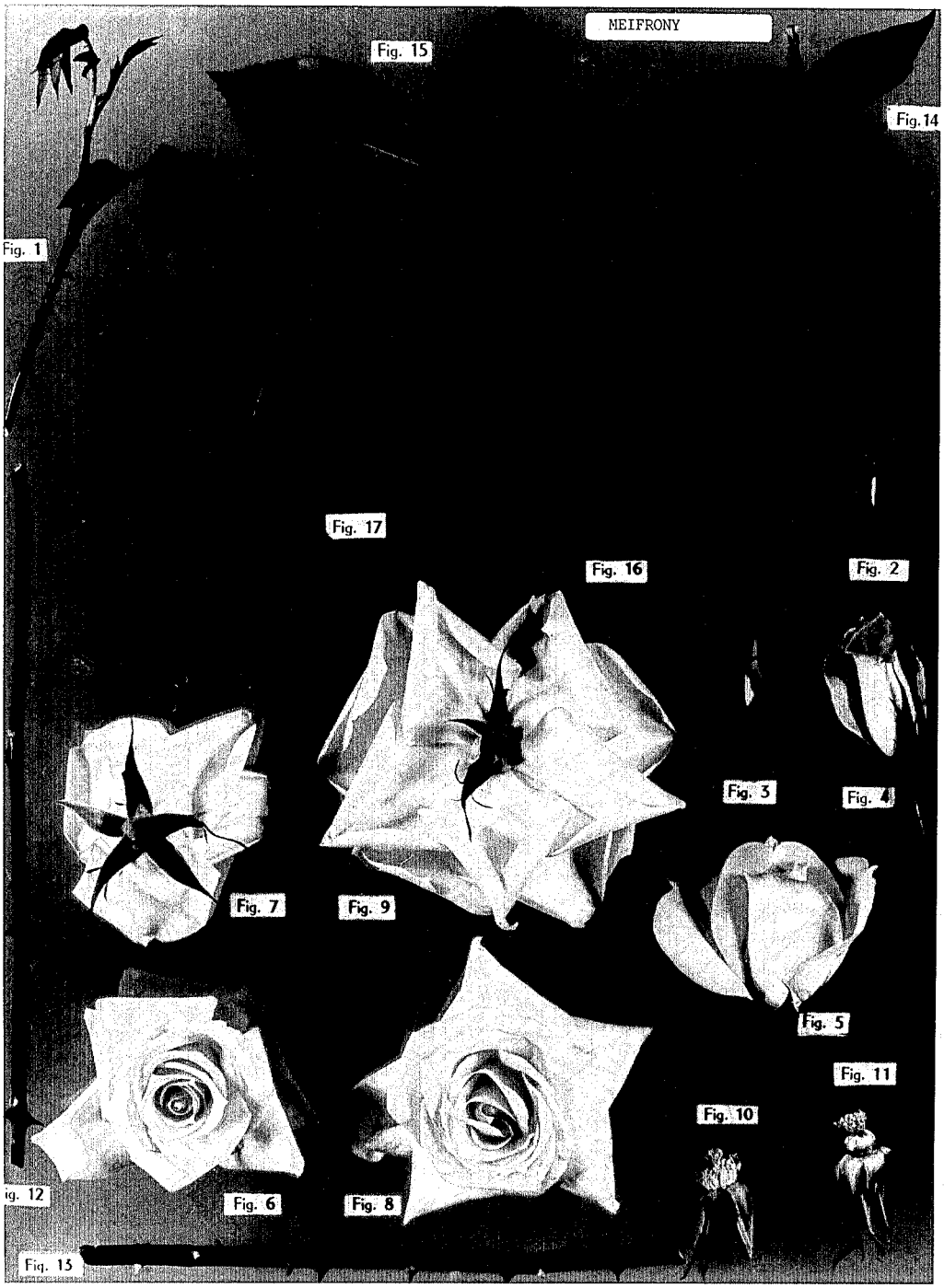
FIG. 1 illustrates a specimen of a young shoot.
FIG. 2 illustrates a specimen of a floral bud before the opening of the sepals.
FIG. 3 illustrates a specimen of a floral bud when the sepals open.
FIG. 4 illustrates a specimen of a floral bud when the petals open.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 13 illustrates a specimen of a section of a main branch.
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.
FIG. 17 illustrates a specimen of a leaf with nine leaflets — plan view — under surface.

The chart used in the identification of the colors is that of The Royal Horticultural Society (R.H.S. Colour Chart). The description is based on observations of two year old specimens made during November while grafted on *Rosa indica* understock and growing in greenhouses at Cap d'Antibes, France. Color terminology in common terms precedes the reference to such chart.

Class: Hybrid Tea.

Plant:

*Height.*—Plants which were pruned to a height of 85 cm. commonly produce floral stems having a length of approximately 50 to 80 cm.

*Habit.*—Upright.

Branches:

*Color.*—Young stems: medium green, Yellow-Green Group 146B. Adult wood: medium green, Green Group 138B.

*Thorns.*—Size: medium to large. Quantity: low to average. Color: pinkish on young stems and greenish changing to tan on adult wood.

Leaves:

*Stipules.*—Adnate, pectinate, somewhat wide and linear.

*Petioles.*—Upper Surface: striped reddish brown on young foliage and medium green on adult foliage with more or less glandular edges. Under surface: light green, smooth.

*Leaflets.*—Number: 3, 5, 7 (most often), and sometimes 9. Shape: spear-like. Serration: single and regular. Texture: consistent. General appearance: dense and bright foliage. Color (young foliage): Upper surface: medium green, Yellow-Green Group 146B, widely stained with reddish coloration. Under surface: reddish brown. Color (adult foliage): Upper Surface: dark green, Green Group 137A. Under surface: medium green, Green Group 138B.

Inflorescence:

*Number of flowers.*—Generally one per stem.

*Peduncle.*—Medium green in coloration, smooth, approximately 7 to 9 cm. in length on average.

*Sepals.*—Upper Surface: tomentose, greenish in coloration. Under Surface: light green in coloration, the outside sepals have edges which are more or less appendiculated ending with a more or less developed leaflike appendix at the tip.

*Buds.*—Shape: conical and elongated. Length: approximately 4 to 4.5 cm. on average. Size: large. Color upon opening: Upper Surface: Venetian pink, Red Group 49C, suffused and edged with light carmine rose, Red Group 52C. Under surface: Orient pink, Red Group 36B, suffused and edged with light neyron rose, Red Group 55A.

*Flower.*—Shape: cuplike. Diameter: approximately 13 cm. on average. Color (when opening begins): Upper surface: Venetian pink, Red Group 49C, suffused and edged with light carmine rose, Red Group 52C. Under surface: orient pink, Red Group 36B, suffused and edged with light neyron rose, Red Group 55A. Color (when blooming): Upper surface: French rose, Red Group 49D, edged and suffused with Carmine Rose, Red Group 52C. Under surface: whitish edged with light neyron rose, Red Group 55A. Color (at end of opening): upper surface: French rose, Red Group 49D, edged and suffused with carmine rose, Red Group 52C. Under surface: whitish edged with light neyron rose, Red Group 55A. Fragrance: none. Lasting quality: long when cut and present in a vase. Petal number: approximately 19 on average. Petal form: generally rounded, sometimes with an asymmetric pin-like base. Texture: consistent. Petal drop: good. Stamen number: approximately 120 to 127 on average. Anthers: normal, strawlike and edged with ochre in coloration, located below the pistils. Filaments: greenish in coloration, of irregular heights. Pistils: approximately 86 to 93 on average. Stigmas: normal, strawlike in coloration. Styles: dark fuchsine in coloration, more or less twisted, tomentose at the base, of irregular heights. Receptacle: medium green in coloration and in longitudinal section in the shape of a funnel.

Development:

*Vegetation.*—Very vigorous.

*Blooming.*—Very floriferous.

*Aptitude to forcing.*—Excellent greenhouse forcing capability.

*Resistance to diseases.*—Good.

I claim:

1. A new and distinct variety of Hybrid Tea rose plant characterized by the following combination of characteristics:

(a) forms elegant conical and elongated buds,
(b) forms in abundance semi-double blossoms which are French rose in coloration and edged and suffused with neyron rose,
(c) exhibits an upright growth habit,
(d) forms vigorous vegetation,
(e) is well adapted for greenhouse forcing,
(f) exhibits good resistance to cryptogamic diseases;

substantially as herein shown and described.

* * * * *

MEIFRONY